(12) United States Patent
Greuter et al.

(10) Patent No.: US 10,905,445 B2
(45) Date of Patent: Feb. 2, 2021

(54) ADJUSTABLE CUTTING BLOCK FOR KNEE ARTHROPLASTY

(71) Applicant: ZIMMER GMBH, Winterthur (CH)

(72) Inventors: Daniel Greuter, Kefikon (CH); Lukas Riedi, Winterthur (CH)

(73) Assignee: ZIMMER GMBH, Winterthur (CH)

( * ) Notice: Subject to any disclaimer, the term of this patent is extended or adjusted under 35 U.S.C. 154(b) by 282 days.

(21) Appl. No.: 15/959,845

(22) Filed: Apr. 23, 2018

(65) Prior Publication Data

US 2018/0325530 A1 Nov. 15, 2018

Related U.S. Application Data

(60) Provisional application No. 62/504,759, filed on May 11, 2017.

(51) Int. Cl.
| | | |
|---|---|---|
| *A61B 17/15* | (2006.01) | |
| *A61B 17/17* | (2006.01) | |
| *A61B 17/56* | (2006.01) | |
| *A61B 17/16* | (2006.01) | |
| *A61B 17/00* | (2006.01) | |

(52) U.S. Cl.
CPC ........ *A61B 17/1764* (2013.01); *A61B 17/155* (2013.01); *A61B 17/164* (2013.01); *A61B 2017/00367* (2013.01)

(58) Field of Classification Search
CPC . A61B 17/155; A61B 17/164; A61B 17/1764; A61B 2017/00367
USPC ................. 606/87–89, 96–98, 104
See application file for complete search history.

(56) References Cited

U.S. PATENT DOCUMENTS

| | | |
|---|---|---|
| 5,486,178 A | 1/1996 | Hodge |
| 5,624,444 A | 4/1997 | Wixon et al. |
| 5,662,656 A | 9/1997 | White |
| 5,810,829 A | 9/1998 | Elliott et al. |

(Continued)

FOREIGN PATENT DOCUMENTS

WO 2018206765 11/2018

OTHER PUBLICATIONS

"International Application Serial No. PCT EP2018 062208, International Preliminary Report on Patentability dated Nov. 21, 2019", 9 pages.

(Continued)

*Primary Examiner* — Jessica Weiss
(74) *Attorney, Agent, or Firm* — Schwegman Lundberg & Woessner, P.A.

(57) ABSTRACT

According to one example, an adjustable cut guide for resecting a bone can include a base, a cam, an actuator, and an insert. The base can include a channel extending between a first end and a second end and a slot intersecting the channel. The cam can extend into the slot, and the cam can be coupled to the base within the slot to rotate between a first position and a second position. The actuator can be disposed in the slot, where the actuator can be translatable by rotation of the cam between an extended position when the cam is in the first position and a retracted position when the cam is in the second position. The insert can be disposed within the channel of the base and the insert can be secured relative to the base by the actuator when the actuator is in the extended position.

19 Claims, 17 Drawing Sheets

(56) References Cited

U.S. PATENT DOCUMENTS

| | | | |
|---|---|---|---|
| 5,910,143 A * | 6/1999 | Cripe | A61B 17/155 |
| | | | 606/86 R |
| 6,013,081 A | 1/2000 | Burkinshaw et al. | |
| 6,059,788 A | 5/2000 | Katz | |
| 6,575,980 B1 | 6/2003 | Robie et al. | |
| 7,104,996 B2 | 9/2006 | Bonutti | |
| 7,621,920 B2 | 11/2009 | Claypool et al. | |
| 8,187,280 B2 | 5/2012 | May et al. | |
| 8,372,080 B2 | 2/2013 | May | |
| 8,506,571 B2 | 8/2013 | Chana et al. | |
| 8,702,714 B2 | 4/2014 | Martin et al. | |
| 9,084,612 B2 | 7/2015 | Sordelet et al. | |
| 9,204,897 B2 | 12/2015 | Jones et al. | |
| 2007/0173848 A1 | 7/2007 | Lennox et al. | |
| 2008/0195109 A1 | 8/2008 | Hunter et al. | |
| 2011/0046629 A1 | 2/2011 | Green et al. | |
| 2013/0204259 A1* | 8/2013 | Zajac | A61B 17/154 |
| | | | 606/88 |
| 2014/0228963 A1* | 8/2014 | Bonutti | A61B 17/025 |
| | | | 623/20.15 |
| 2014/0276837 A1* | 9/2014 | Chaney | A61B 17/1675 |
| | | | 606/80 |
| 2016/0015399 A1 | 1/2016 | Chaney et al. | |

OTHER PUBLICATIONS

"International Application Serial No. PCT EP2018 062208, International Search Report dated Jul. 31, 2018", 7 pgs.
"International Application Serial No. PCT EP2018 062208, Written Opinion dated Jul. 31, 2018", 7 pgs.

* cited by examiner

ADJUSTABLE CUTTING BLOCK FOR KNEE ARTHROPLASTY

CLAIM OF PRIORITY

This application claims the benefit of U.S. Provisional Patent Application Ser. No. 62/504,759, filed on May 11, 2017, the benefit of priority of which is claimed hereby, and which is incorporated by reference herein in its entirety.

FIELD

The present subject matter relates to orthopedic prostheses and, more particularly, to prostheses, systems and methods used in knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial bearing component and a tibial component implanted on the proximal end of a tibia to replicate the function of a healthy natural knee. Various types of arthroplasties are known including a total knee arthroplasty, where all of the articulating compartments of the joint are repaired with prosthetic components.

OVERVIEW

This disclosure pertains generally to knee prostheses, systems, and methods for a knee arthroplasty and/or as part of a knee revision surgery. The present inventors have recognized, among other things, that patients requiring knee arthroplasties can have femurs of varying qualities, such as size, density, and condition/health. Because of these variations, location and depth of cuts performed on the bones may vary relatively dramatically between patients. Because it may be expensive to match cutting guide specific to each patient, a system that is adjustable is desired to guide a bone cut for a variety of patients.

Thus, the present inventors propose a cutting block that includes an insert translatable within a channel of the block. The cutting block can also include a cam rotatable within the base to operate an actuator to secure the insert relative to the block when the cam is in a first position and can allow the insert to translate within the channel of the block when the insert is in the second position. These features can allow the block to be quickly and easily adjusted (and readjusted) to select a cutting location as desired.

To further illustrate the apparatuses and systems disclosed herein, the following non-limiting examples are provided:

In Example 1, an adjustable cut guide for resecting a bone can include a base, a cam, an actuator, and an insert. The base can include a channel extending between a first end and a second end and a slot intersecting the channel. The cam can extend into the slot, and the cam can be coupled to the base within the slot to rotate between a first position and a second position. The actuator can be disposed in the slot, where the actuator can be translatable by rotation of the cam between an extended position when the cam is in the first position and a retracted position when the cam is in the second position. The insert can be disposed within the channel of the base, the insert can be secured relative to the base by the actuator when the actuator is in the extended position, and the base can be translatable relative to the insert within the channel when the actuator is in the retracted position.

In Example 2, the subject matter of Example 1 optionally includes wherein: the insert further comprises a rack including rack teeth; and the actuator further comprises teeth engageable with the rack teeth to secure the insert to the base when the actuator is in the extended position.

In Example 3, the subject matter of Example 2 optionally includes wherein the teeth of the actuator disengage the rack teeth when the actuator is in the retracted position such that the base is free to move relative to the insert.

In Example 4, the subject matter of Example 3 optionally includes the channel further comprising: a track configured to receive the rack of the insert, wherein the actuator teeth extend into the track to engage the rack when the actuator is in the extended position.

In Example 5, the subject matter of any one or more of Examples 1-4 optionally include a biasing element engaging the actuator and the base within the slot, the biasing element biasing the actuator to an extended position and the cam to the first position.

In Example 6, the subject matter of any one or more of Examples 1-5 optionally include wherein the actuator further comprises a leg extending away from the cam into an anti-rotation slot of the block, the leg translatable in the slot with the actuator and the slot limiting rotation of the leg about an axis of the actuator.

In Example 7, the subject matter of any one or more of Examples 1-6 optionally include wherein the insert further comprises a first intramedullary bore disposed proximate an anterior portion of the insert and a second intramedullary bore disposed proximate a posterior portion of the insert.

Example 8 is a guide assembly for resecting a femur for a knee arthroplasty, the assembly comprising: a cut guide comprising: a base comprising: a channel extending between a first end and a second end; a slot intersecting the channel; a cam extending into the slot, the cam coupled to the base within the slot to rotate between a first position and a second position; an actuator disposed in the slot engageable with the cam, the actuator translatable by rotation of the cam between an extended position when the cam is in the first position and a retracted position when the cam is in the second position; and an insert comprising an intramedullary bore, the insert engageable within the channel of the base, the insert secured relative to the base by the actuator when the actuator is in the extended position, and the base translatable relative to the insert between the first and second end when the actuator is in the retracted position; and an intramedullary rod insertable into the intramedullary bore of the insert and insertable into an intramedullary cavity of the bone.

In Example 9, the subject matter of Example 8 optionally includes cut guide further comprising: a plurality of bores extending through the base substantially parallel to the intramedullary bore.

In Example 10, the subject matter of any one or more of Examples 8-9 optionally include the cut guide further comprising: an intramedullary bore configured to receive an intramedullary rod therethrough, the intramedullary rod insertable into an intramedullary canal of the bone; and wherein the channel is configured to accept a plurality of inserts including the insert, wherein each of the plurality of inserts comprises an intramedullary rod bore having a rod angle between 1 degree and 9 degrees.

In Example 11, the subject matter of any one or more of Examples 8-10 optionally include wherein the cut guide is an anterior/posterior cutting block for resection of a distal portion of a femur.

In Example 12, the subject matter of any one or more of Examples 8-11 optionally include wherein translation of the base relative to the insert and the intramedullary rod provides an anterior to posterior adjustment of the base relative to the bone.

In Example 13, the subject matter of any one or more of Examples 8-12 optionally include the body further comprising: a plurality of pin apertures extending through the body configured to receive pins therethrough to fixate the base to the bone.

In Example 14, the subject matter of any one or more of Examples 8-13 optionally include wherein the body is configured to receive at least one of a ligament tensioner and an anterior outrigger.

Example 15 is a method of inserting an intramedullary guide rod into a bone, the method comprising: actuating a cam to retract an actuator; inserting an angle guide into a slot of the body of the guide; inserting an intramedullary rod through a bore of the angle guide and into an intramedullary cavity of the bone; and releasing the cam to extend the actuator to secure the angle guide relative to the body.

In Example 16, the subject matter of Example 15 optionally includes translating the body relative to the intramedullary rod and the angle guide to anteriorly to posteriorly adjust the body relative to the bone.

In Example 17, the subject matter of any one or more of Examples 15-16 optionally include inserting one or more pins through pin apertures of the body to secure the body to the bone.

In Example 18, the subject matter of any one or more of Examples 15-17 optionally include coupling a ligament tensioner to the body; and operating the tensioner to set a ligament tension of a joint of the bone.

In Example 19, the subject matter of any one or more of Examples 17-18 optionally include coupling a cutting guide to the body; inserting a cutting blade through the guide to engage the bone; and operating the cutting blade to resect the bone.

In Example 20, the subject matter of any one or more of Examples 15-19 optionally include spacing an anterior cutting guide on an anterior portion of the bone by coupling an outrigger to the anterior cutting guide and to the body.

In Example 21, the cutting block, assembly, or method of any one of or any combination of Examples 1-20 is optionally configured such that all elements or options recited are available to use or select from.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and methods for a knee arthroplasty, where a tibia and/or a femur are resected to receive prostheses to replace damaged or nonfunctioning components of a patient.

As used herein, the terms "proximal" and "distal" should be given their generally understood anatomical interpretation. The term "proximal" refers to a direction generally toward the torso of a patient, and "distal" refers to the opposite direction of proximal, i.e., away from the torso of a patient. It should be understood that the use of the terms "proximal" and "distal" should be interpreted as though the patient were standing with the knee joint in extension despite the apparatuses described herein generally being used with the knee joint in flexion. The intent is to differentiate the terms "proximal" and "distal" from the terms "anterior" and "posterior". As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior".

Figure 1:
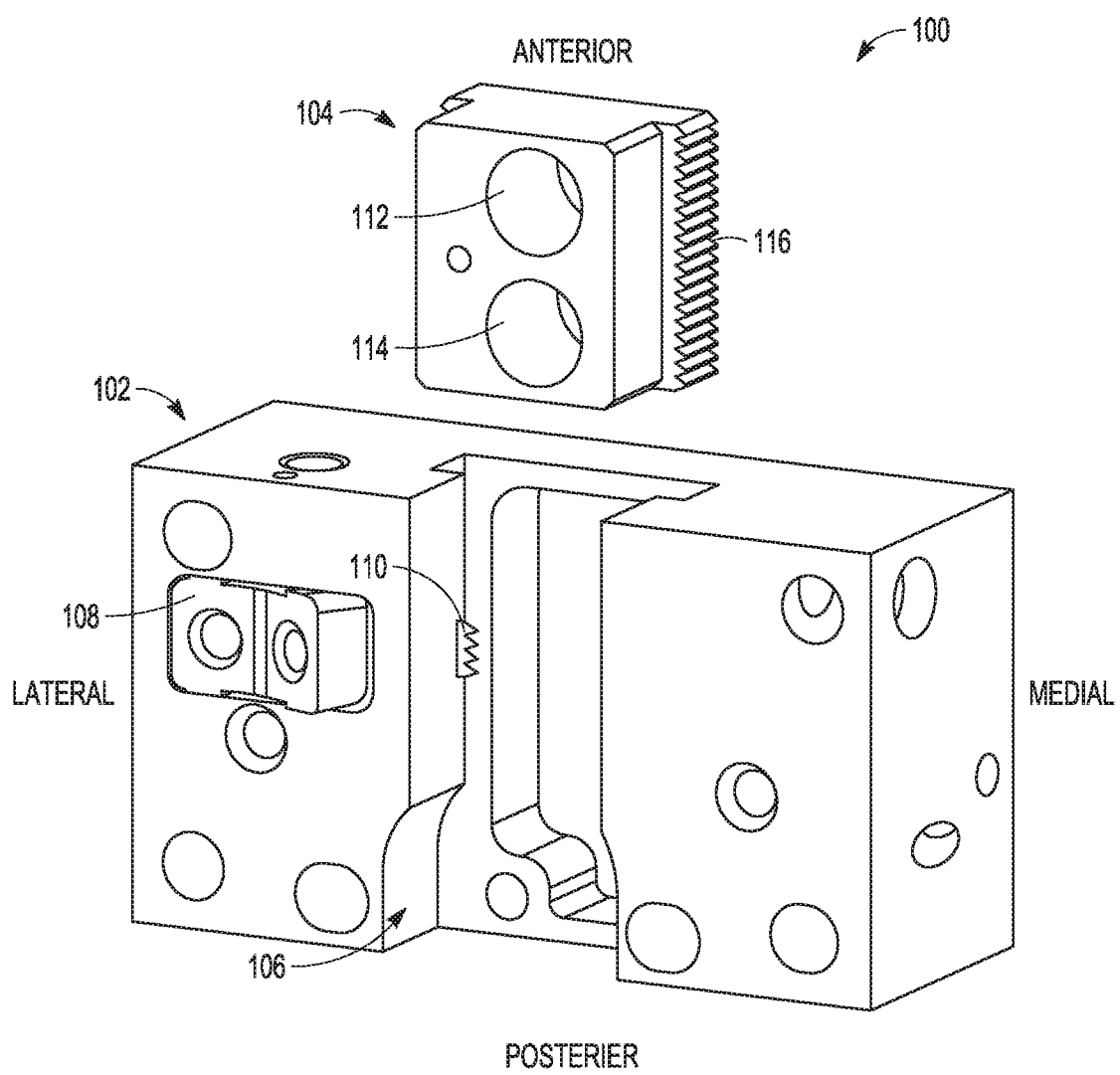
FIG. 1 shows an isometric view of a cutting guide assembly, in accordance with at least one example of the present disclosure.

FIG. 1 shows an isometric view of cutting guide assembly 100, in accordance with at least one example of the present disclosure. Cutting guide assembly 100 can include base 102 and insert 104. Base 102 can include channel 106, cam 108, and actuator 110. Insert 104 can include anterior intramedullary (IM) bore 112, posterior IM bore 114, and rack 116. Also shown in FIG. 1 are orientation indicators Anterior, Posterior, Medial, and Lateral.

Base 102 and insert 104 can be rigid members comprised of materials such as plastics, metals, and combinations thereof. For example, base 102 and insert 104 can be comprised of steel alloys. Insert 104 (or angle guide) can be insertable into base 102, as described further below.

Channel 106 can be a channel extending between an anterior portion and a posterior portion of base 102. Channel 106 can be sized to receive insert 104 such that insert 104 can translate therein. Channel 106 can include an undercut or track (discussed further below) configured to receive rack 116 of insert 104.

Cam 108 can be a rigid member comprised of materials such as metals, plastics, and combinations thereof. Cam 108 can be pivotably coupled to base 102 and can engage actuator 110. Actuator 110 can be a rigid member comprised of materials such as metals, plastics, and combinations thereof. Actuator 110 can be disposed in a slot of base 102 (as discussed further below), where the slot intersects channel 106, such that actuator 110 can extend into channel 106 when actuator 110 is in a first position, as shown in FIG. 1. Actuator 110 can include teeth configured to engage teeth of rack 116, as discussed further below.

Insert 104 can include anterior IM bore 112 and posterior IM bore 114, where each bore can extend through the insert generally perpendicular to the anterior/posterior plane. Insert 104 can also include rack 116, which can be a rack type gear including teeth configured to extend from a medial and a lateral portion of insert 104 (only medial teeth visible in FIG. 1) to face medially and laterally, respectively.

In operation of some examples, cam 108 can be rotated clockwise (as shown further below) to retract actuator 110 into base 102. Insert 104 can then be inserted into channel 106 such that rack 116 is disposed in the track of channel 106. Cam 108 can then be released so that a biasing element within base 102 can force actuator 110 medially to enter the track of channel 106 to engage lateral teeth of insert 104. This engagement can secure the position of insert 104 relative to base 102.

Thereafter, (as shown further below) an intramedullary (IM) rod can be inserted through one of anterior IM bore 112 or posterior IM bore 114 to secure cutting guide assembly 100 to the IM rod and therefore the bone. By including two bores (112 and 114) in insert 104, the IM rod can be aligned near posterior and anterior terminations of base 102. In some examples, cutting guide assembly can be used for both left and right knees by rotating the insert about 180 degrees.

Then, cam 108 can be actuated again to allow base 102 to move relative to insert 104. Base 102 can be aligned with the bone and cam 108 can be again released, allowing actuator 110 to secure base 102 to insert 104 and therefore secure base 102 relative to the IM rod and the bone. The details of the operations are discussed below in further detail.

By including cam 108 and actuator 110, cut guide assembly 100 offers a base that is easily adjusted relative to insert 104 when insert 104 is secured to an IM rod. This can allow for simpler and easier adjustments of base 102 and insert 104 during arthroplasty procedures, which can save time and cost.

Figure 2:
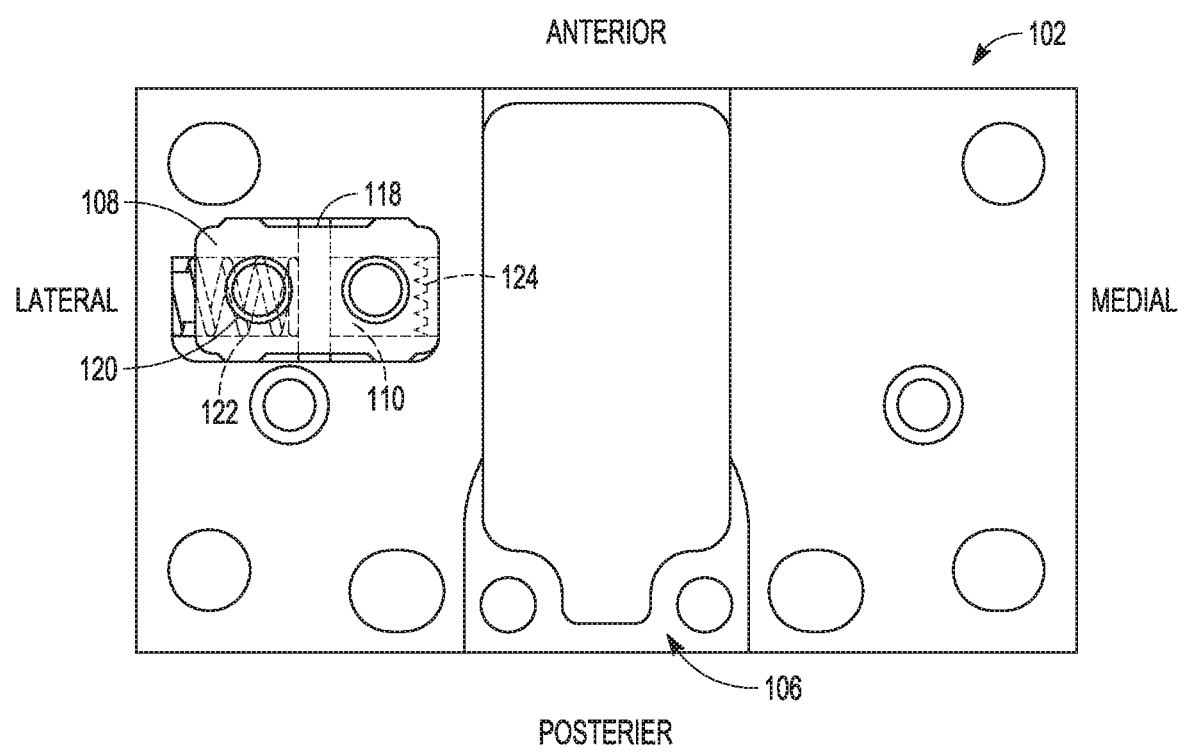
FIG. 2 shows a plan view of a cutting guide assembly, in accordance with at least one example of the present disclosure.

FIG. 2 shows a plan view from a slightly anterior perspective of cutting guide assembly 100, in accordance with at least one example of the present disclosure. Cutting guide assembly 100 can include base 102, which can include channel 106, cam 108, actuator 110, cam pin 118, biasing element 120, and slot 122. Actuator 110 can include teeth 124. Also shown in FIG. 2 are orientation indicators Anterior, Posterior, Medial, and Lateral.

Cutting guide assembly 100 can be consistent with the description of FIG. 1 above; however, FIG. 2 shows additional details of cutting guide assembly 100. For example, cam 108 is shown as being coupled to base 102 by cam pin 118. Cam pin 118 can be a generally cylindrical rigid member comprised of materials such as metals, plastics, and combinations thereof. Cam pin 118 can be secured to base 102 at two respective ends and can pass through a bore of cam 108 to form a journal bearing about which cam 108 can rotate, in some examples.

Also shown in FIG. 2 is slot 122, which can house cam 108, actuator 110 and biasing element 120. In some examples, slot 122 can be of multiple sizes where a larger portion can support actuator 108 and a smaller portion can support actuator 110 and biasing element 120. Slot 122 can intersect with channel 106, as shown below in further detail.

Biasing element 120 can be a resilient member configured to bias actuator 110 medially from slot 122 to extend partially into channel 106. In some examples, biasing element 120 can be a compression spring, such as a coil compression spring or a wave spring. In some other examples, biasing element 120 can be other types of resilient members, such as a resilient plastic or rubber elements.

Also shown in FIG. 2 is actuator 110, which can be a rigid member extending most of the lateral to medial length of slot 122. Actuator 110 can also include teeth 124, which can be disposed at a medial termination of actuator 110 facing medially outward from actuator 110, such that teeth 124 can extend into channel 106 when actuator 110 is in the first position (as shown in FIG. 1) and can be retracted into slot 122 when actuator 110 is in the second position (as shown in FIG. 2).

Figure 3A:
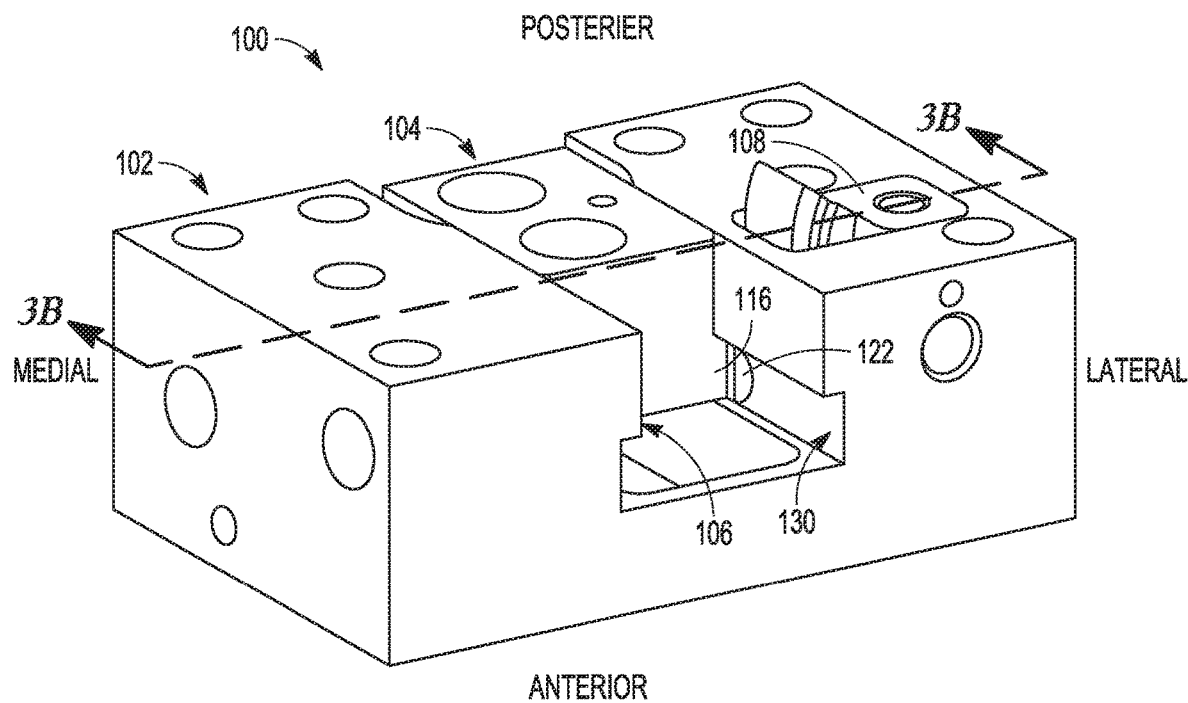
FIG. 3A shows an isometric view of a cutting guide assembly in a first condition, in accordance with at least one example of the present disclosure.
Figure 3B:
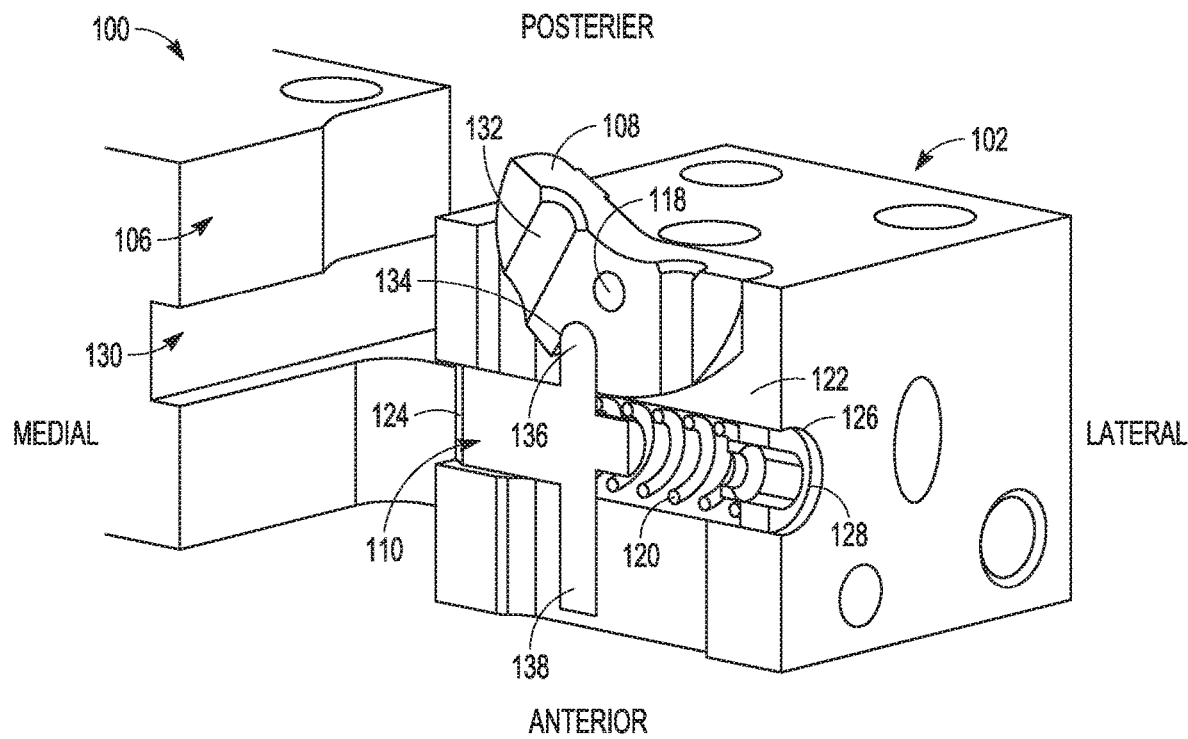
FIG. 3B shows a cross-section view of a cutting guide assembly across section 3B-3B of FIG. 3A in a first condition, in accordance with at least one example of the present disclosure.

FIG. 3A shows an isometric view of cutting guide assembly 100 in a first condition, in accordance with at least one example of the present disclosure. FIG. 3B shows a cross-section view of cutting guide assembly 100 across section 3B-3B of FIG. 3A in a first condition, in accordance with at least one example of the present disclosure. FIGS. 3A and 3B are discussed below concurrently.

Cutting guide assembly 100 can include base 102 and insert 104 (only shown in FIG. 3A). Base 102 can include channel 106, cam 108, actuator 110 (only shown in FIG.

3B), cam pin 118 (only visible in FIG. 3B), biasing element 120 (only visible in FIG. 3B), slot 122, actuator bore 126 (only visible in FIG. 3B), and actuator plug 128 (only visible in FIG. 3B). Channel 106 can include track 130. Cam 108 can include bores 132 and notch 134. Actuator 110 can include teeth 124, cam arm 136 and alignment arm 138. Insert 104 can include rack 116. Also shown in FIGS. 3A and 3B are orientation indicators Anterior, Posterior, Medial, and Lateral.

Cutting guide assembly 100 can include slot 122, which can extend through base 100 substantially perpendicular to the anterior-posterior plane. Slot 122 can be sized to support cam 108 and actuator 110. Actuator bore 126 can be a bore extending from a lateral termination of base 102, intersecting slot 122 and intersecting with and terminating at channel 106. In some examples, actuator bore 126 can be sized to support actuator 110, biasing element 120, and actuator plug 128.

Actuator plug 128 can be a rigid member disposed proximate a lateral termination of actuator bore 126. Actuator plug 128 can be configured to engage biasing element 120 and can be configured to retain biasing element 120 and therefore actuator 110 within actuator bore 126. In some examples, actuator plug 128 can be secured to base 102 in a threaded configuration, and can be pinned, compression fit, welded, and snap fit into actuator bore 126 in other examples.

FIGS. 3A and 3B also show track 130 of channel 106, which can be an undercut extending medially and laterally into base 102. Track 130 can be sized to receive rack 116 of insert 104 (of FIG. 3A) while allowing track 130, and therefore insert 104, to translate within channel 106 and track 130 when actuator 110 does not engage track 130.

Cam 108 can include bores 132, which can extend through cam 108 providing cleaning and sterilization access to internal components of base 102, such as actuator plug 128, biasing element 120, slot 122, and actuator 110. Notch 134 can be a notch in cam 108 substantially facing actuator 110 and sized to receive cam arm 136 of actuator 110.

Cam arm 136 can be a rigid protrusion extending towards cam 108 from actuator 110 and can be configured to engage notch 134 of cam 108. Alignment arm 138 can extend opposite of cam arm 136 from actuator 110 and can terminate prior to extending past base 102. Alignment arm 138 can be sized to fit within slot 122 but sized to engage the walls of channel 122 to reduce rotation of actuator 110 relative to actuator bore 126, helping to ensure that teeth 124 of actuator 110 remain aligned with teeth of track 116.

In operation of some examples, teeth 124 can be disposed at a medial termination of actuator 110, as described above, and can extend into track 130 to engage teeth of rack 116 when actuator 110 is in a first position, as shown in FIGS. 3A and 3B. Because biasing element 120 applies a force to plug 128 and actuator 110, biasing element 120 biases teeth 124 to extend into track 116. Also, because cam arm 136 engages cam 108 at notch 134 of cam 108, biasing element 120 biases cam 108 into the first position as shown in FIGS. 3A and 3B.

While teeth 124 of actuator 110 help prevent translation of insert 104 within slot 106, engagement of rack 116 with surfaces of track 130 and engagement of other portion of insert 104 with surfaces of channel 106 reduce translation or rotation of insert 104 relative to base 102 in any other direction.

Figure 4A:
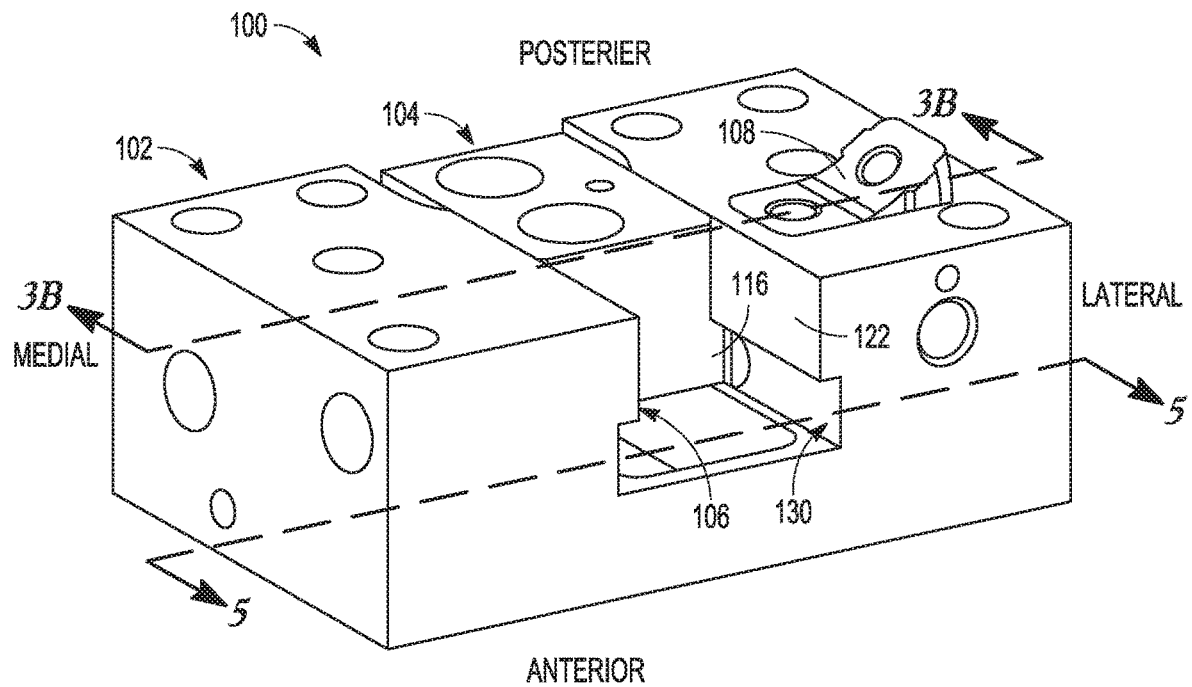
FIG. 4A shows an isometric view of a cutting guide assembly in a second condition, in accordance with at least one example of the present disclosure.
Figure 4B:
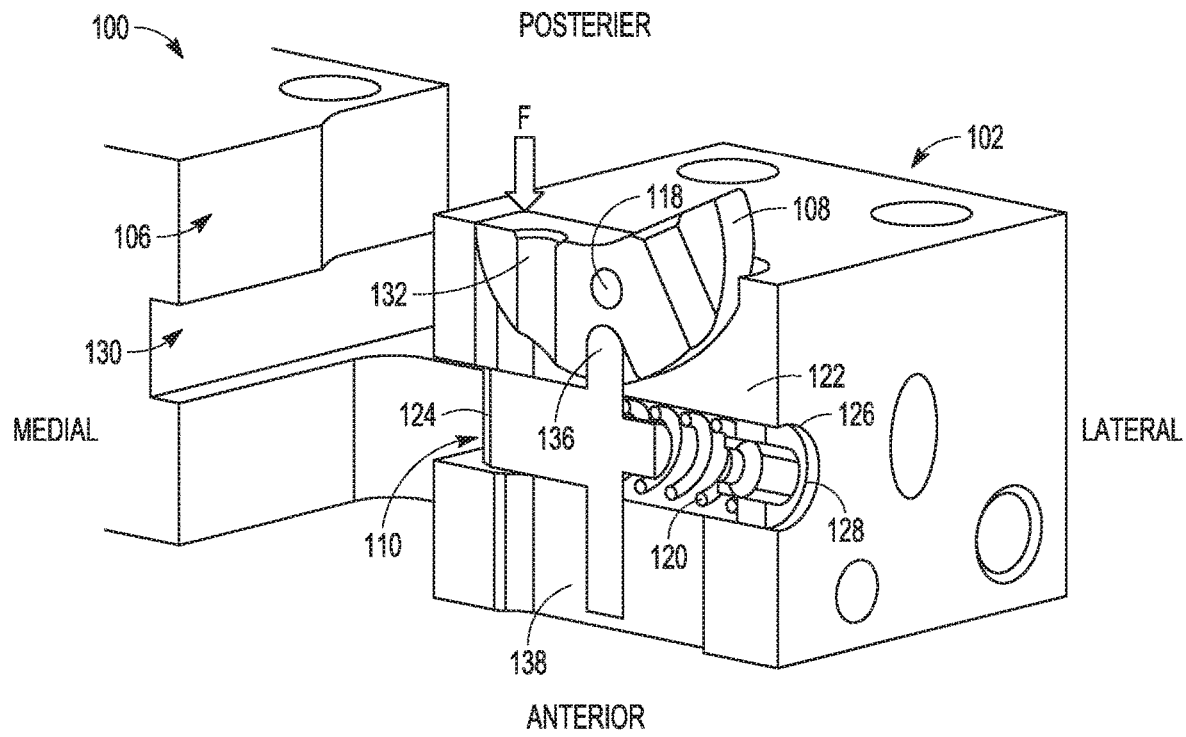
FIG. 4B shows a cross-section view of a cutting guide assembly across section 4B-4B of FIG. 4A in a second condition, in accordance with at least one example of the present disclosure.

FIG. 4A shows an isometric view of cutting block assembly 100 in a second condition, in accordance with at least one example of the present disclosure. FIG. 4B shows a cross-section view of cutting guide assembly 100 across section 4B-4B of FIG. 4A in a second condition, in accordance with at least one example of the present disclosure. FIGS. 4A and 4B are discussed below concurrently. The components of FIGS. 4A and 4B can be consistent with FIGS. 3A and 3B, described above, but can show cutting guide assembly 100 in a second state or condition. FIGS. 4A and 4B also show force F.

In operation of some examples, force F can be applied to cam 108, rotating cam 108 about cam pin 118 in a counterclockwise direction (as orientated in FIG. 4B), which can cause cam 108 to move to a second position. Rotation of cam 108 can also cause cam arm 136 and therefore actuator 110 to translate medially, compressing biasing element 120. Medial translation of actuator 110 can cause teeth 124 to translate in actuator bore 126 out of track 130 of channel 106 such that teeth 124 will disengage rack 116 of insert 104. This can allow insert 104 to be translated anteriorly to posteriorly within channel 106 (or base 102 to translate relative to insert 104).

In some examples, when force F is removed from cam 108, or when force F is reduced so that a biasing force of biasing element 120 overcomes force F, biasing element 120 can motivate actuator 110 to translate laterally, which can cause cam 108 to rotate about cam pin 118 in a clockwise direction (as orientated in FIG. 4B) toward the first position of cam 108 (as shown in FIGS. 3A and 3B). Because actuator 110 is biased to the first position, base 102 and insert 104 can be secured to each other without continued application of a force external to cutting guide assembly 100 (such as force F).

Figure 5:
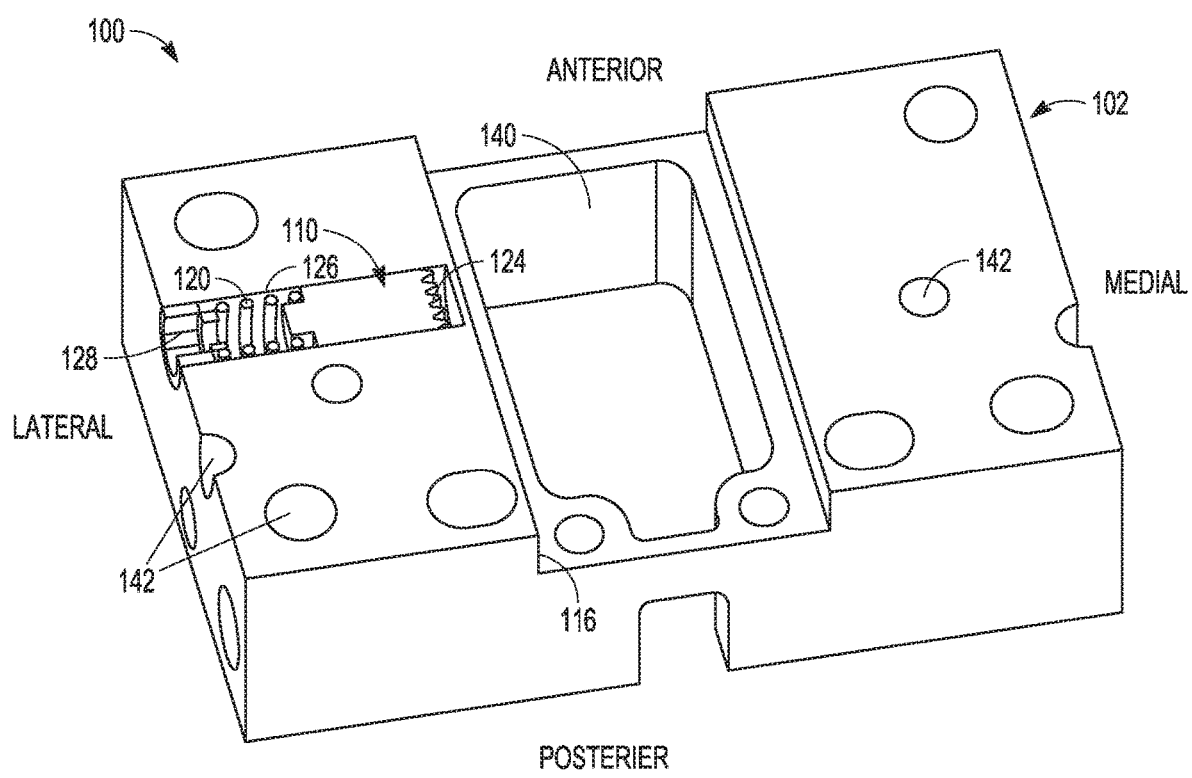
FIG. 5 shows a cross-section view of a cutting guide assembly across section 5-5 of FIG. 4A in a second condition, in accordance with at least one example of the present disclosure.

FIG. 5 shows a cross-section view of cutting guide assembly 100 across section 5-5 of FIG. 4A in a second condition, in accordance with at least one example of the present disclosure. Cutting guide assembly 100 can include base 102, actuator 110, track 116, biasing element 120, actuator bore 126, and plug 128. Actuator 110 can include teeth 124. Base 102 can include central opening 140 and pin bores 142.

Cutting guide assembly 100 as shown in FIG. 5 can be consistent with the description of the FIGS. above. However, FIG. 5 more clearly shows that biasing element 120 can be disposed around a posterior portion of actuator 110 and a medial portion of plug 128. FIG. 5 also shows how teeth 124 of actuator 110 are retracted out of track 116 and into actuator bore 126 when actuator 110 is in the second position.

Central opening 140 can be an opening extending through an approximately central portion of base 102. Central opening 140 can have a geometric shape that is substantially rectangular, in some examples, but can include non-regular aspects, such as rounded corners and notches. In some examples, central opening 140 can be placed to align with IM bores of the insert when the insert is inserted into channel 106 of base 102.

Pin bores 142 can also extend through base 102. Pin bores 142 can be sized to receive and guide drill bits through base 102. Pine bores 142 can also be sized to receive pins, such as Steinmann pins, in some examples, to temporarily secure base 102 to a bone, such as a femur, as discussed further below.

Figure 6A:
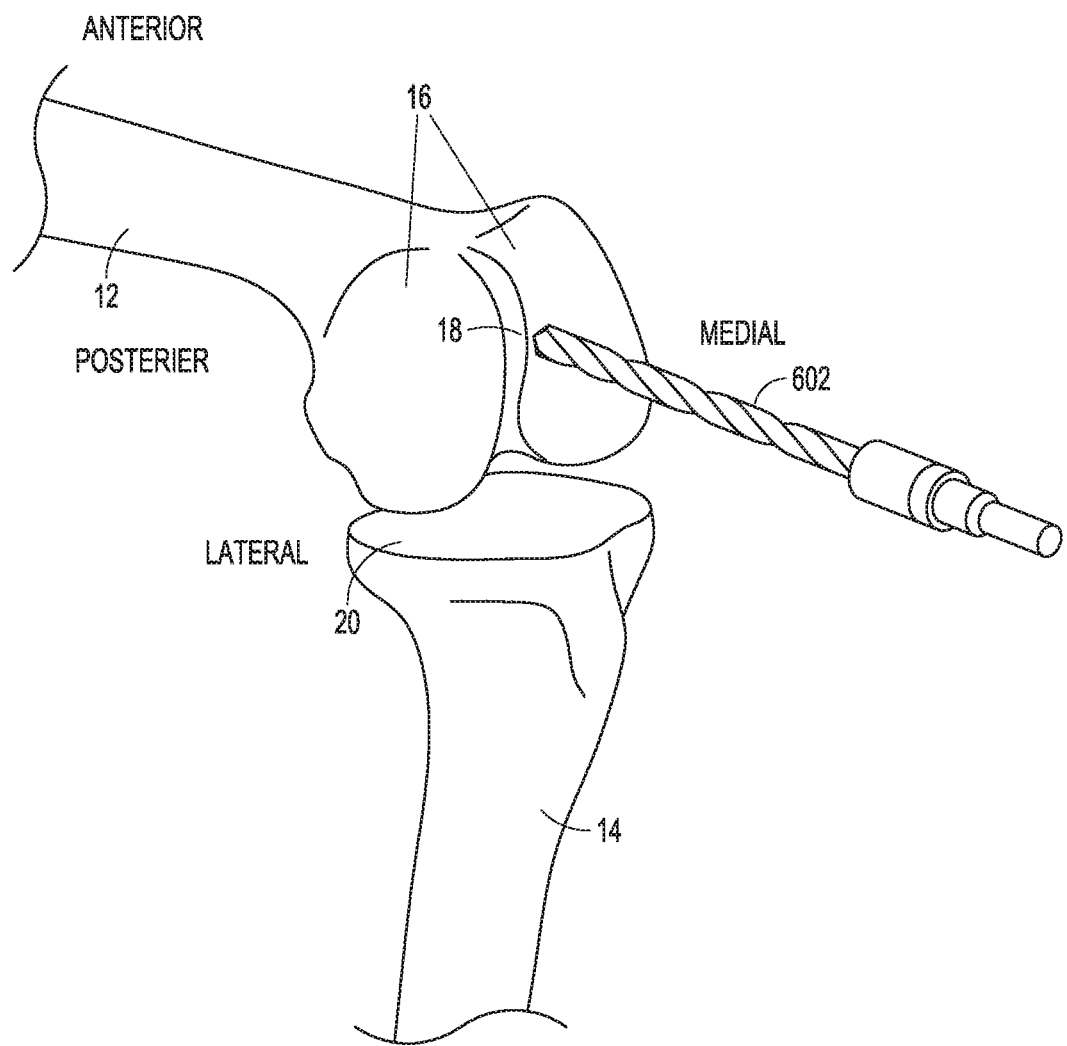
FIG. 6A shows an isometric view of a femur and a tibia, in accordance with at least one example of the present disclosure.
Figure 6B:
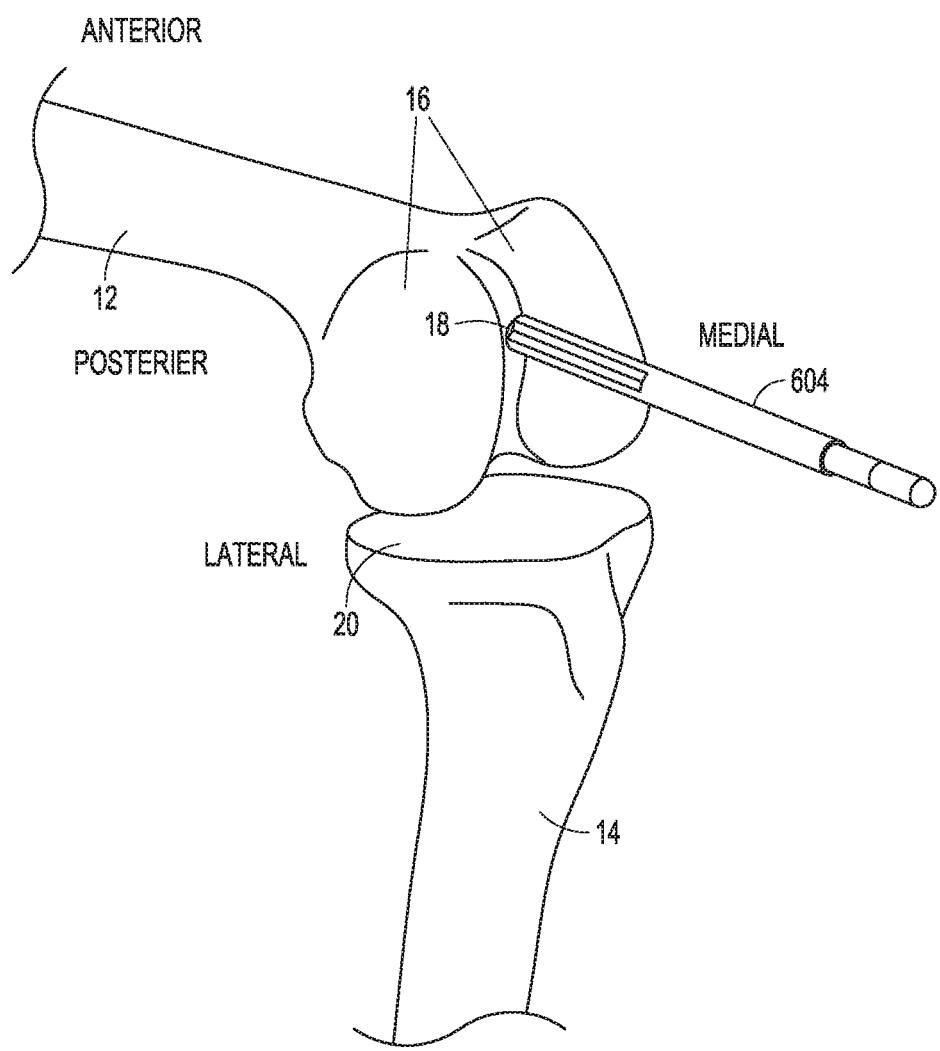
FIG. 6B shows an isometric view of a femur and a tibia with an intramedullary rod installed, in accordance with at least one example of the present disclosure.

FIG. 6A shows an isometric view of femur 12 and tibia 14 where a drilling operation is being performed, in accordance with at least one example of the present disclosure. FIG. 6B shows an isometric view of femur 12 and tibia 14 with intramedullary rod 604 installed, in accordance with at least one example of the present disclosure. FIGS. 6A and 6B are discussed below concurrently.

Femur 12 and tibia 14 can be a femur and tibia, respectfully, of a human leg. Femur 12 can include condyles 16 and intramedullary cavity 18. Tibia 14 can include resected portion 20, which can be resected by operations performed prior to those operations described herein. Also shown in FIG. 6A is drill bit 602, intramedullary (IM) rod 604, and orientation indicators Anterior, Posterior, Medial, and Lateral.

Drill bit 602 can be a component engageable with a rotary device, such as a drill. In some examples, the rotary device can rotate drill bit 602 at speeds sufficiently high to remove material (such as bone) in contact with drill bit 602. In this way, drill bit 602 can create a bore. Drill bit 602 can be comprised of metal alloys and other rigid materials (such as diamond) and combinations thereof.

IM rod 604 can be a rigid member comprised of materials such as metals, plastics, and combinations thereof. IM rod 604 can be configured to be inserted into a bore created by drill bit 602. IM rod 604 can be further inserted into the bore and into intramedullary cavity 18 of femur 12.

In operation of some examples, a drill or other rotary tool (not shown) can be used to create a bore between condyles 16 of femur 12 to expose intramedullary cavity 18, as shown in FIG. 6A. Once intramedullary cavity 18 is exposed, IM rod 604 can be inserted into intramedullary cavity 18, as shown in FIG. 6B. Further operations are detailed in the figures below.

Figure 7A:
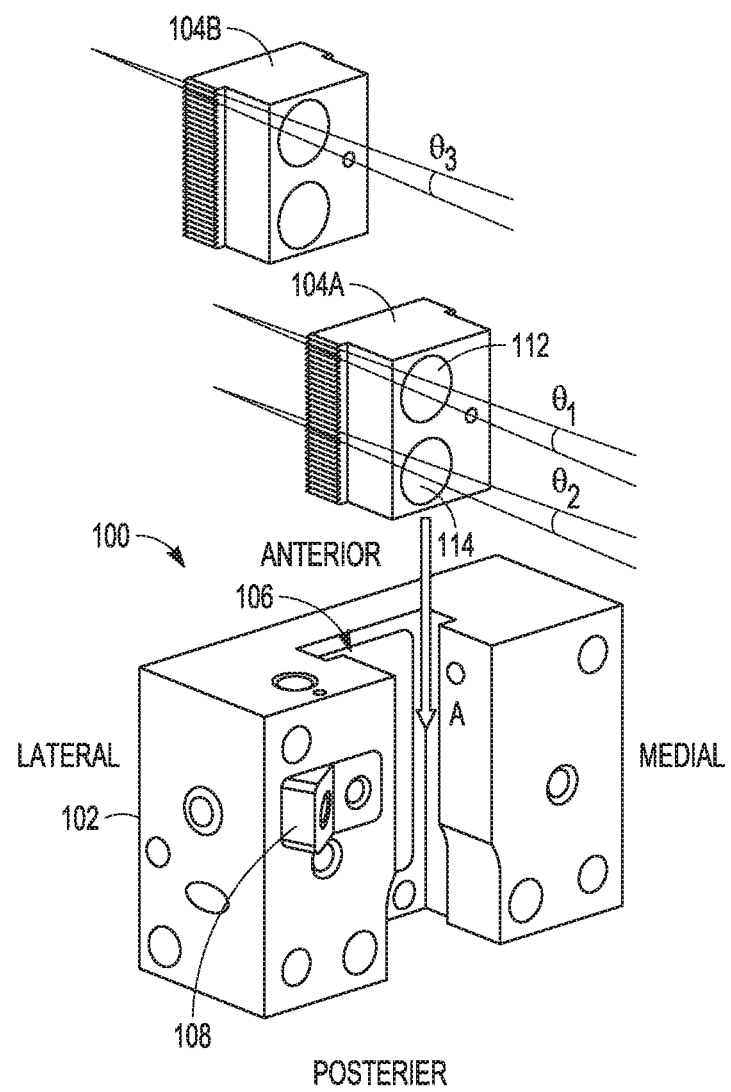
FIG. 7A shows an isometric view of a cutting guide assembly, in accordance with at least one example of the present disclosure.

FIG. 7A shows an isometric view of cutting guide assembly 100, in accordance with at least one example of the present disclosure. FIG. 7A shows arrow A and orientation indicators Anterior, Posterior, Medial, and Lateral. Cutting guide assembly 100 can be consistent with the above description of cutting guide assembly 100 in FIGS. 1-5. However, FIG. 7A also shows inserts 104A and 104B, which can both be consistent with the description of insert 104 discussed above. Insert 104A can include angle $\theta_1$ and angle $\theta_2$ and insert 104B can include angle $\theta_3$. Angle $\theta_1$ can represent a first valgus angle, or an angle between a mechanical axis and an anatomical axis of the femur. Angle $\theta_2$ can represent a second valgus angle and angle $\theta_3$ can represent a third valgus angle. In some examples, angle $\theta_1$ and angle $\theta_2$ can be the same angle. In some other examples, angle $\theta_1$ and angle $\theta_2$ can be different angles. In some examples, angle $\theta_1$ and angle $\theta_2$ can be different than angle $\theta_3$.

In operation of some examples, an insert with a desired valgus angle can be selected. The insert, such as insert 104A, can then be inserted into channel 106 in the direction of arrow A, in some examples. In other examples, insert 104A can be inserted into the posterior opening of channel 106 in a direction substantially opposite arrow A. That is, insert 104A can be inserted into channel 106 from either direction.

Once insert 104A is inserted, or during or prior to insert 104A being inserted, cam 108 can be actuated, retracting actuator 110 (not shown in FIG. 7A) out of channel 106, so that insert 104A can be placed as desired into channel 106. Once a location has been selected, cam 108 can be released, allowing actuator 110 to engage insert 104A. The rest of the operations are discussed with respect to the FIGS. below.

Figure 7B:
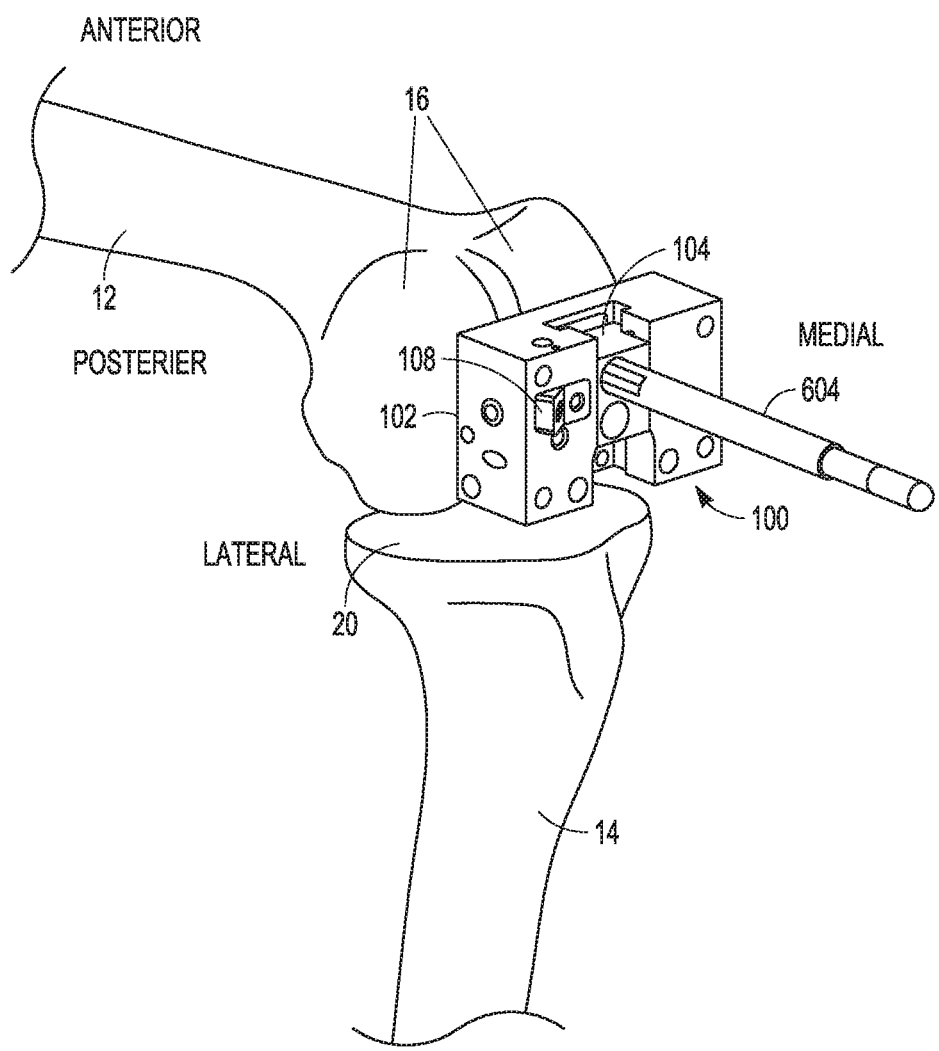
FIG. 7B shows an isometric view of a femur and a tibia with a cutting guide assembly secured to the intramedullary rod, in accordance with at least one example of the present disclosure.

FIG. 7B shows an isometric view of femur 12 and tibia 14 with cutting guide assembly 100 secured to the intramedullary rod 604, in accordance with at least one example of the present disclosure. Cutting guide assembly 100 can be consistent with the above description of cutting guide assembly 100.

In operation of some examples, IM rod 604 can be guided through a central opening of base 102 and through an IM bore (such as bore 112 or 114) of insert 104 to secure cutting guide 100 to IM rod 604.

Figure 8A:
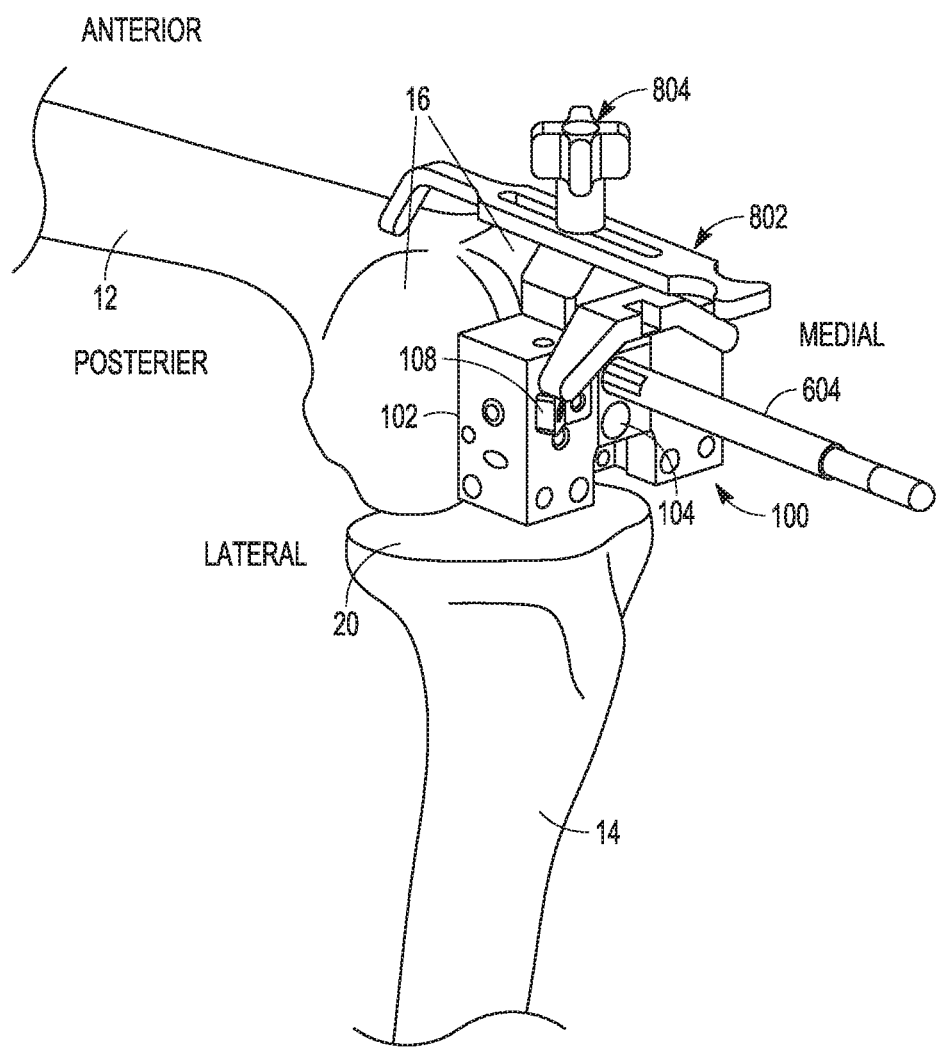
FIG. 8A shows an isometric view of a cutting guide assembly, in accordance with at least one example of the present disclosure.

FIG. 8A shows an isometric view of femur 12 and tibia 14 with cutting guide assembly 100 secured to the intramedullary rod 604 and anterior femoral feeler 802 secured to cutting guide assembly 100, in accordance with at least one example of the present disclosure. Cutting guide assembly 100 can be consistent with the above description of cutting guide assembly 100.

Anterior femoral feeler 802 can be secured to cutting guide assembly and knob 804 can be adjusted to position the feeler relative to femur 12 and condyles 16. Cam 108 can be actuated to retracted actuator 110 (not shown in FIG. 8A), allowing base 102 to translate in the anterior-posterior plane. In some examples, base 102 can be translated anteriorly to reduce an amount of femur 12 that is to be resected from a distal portion of femur 12, whereby anterior femoral feeler 802 can provide an indication of the correct position based on contact between anterior femoral feeler 802 and/or its position relative to femur 12 and condyles 16 thereof. In some other examples, base 102 can be translated posteriorly to increase an amount of femur 12 that is to be resected from a distal portion of femur 12. Once a desired position is selected, cam 108 can be released, allowing the actuator to secure insert 104 to base 102. In some examples, it can be determined that the relative position of insert 104 to base 102 is not desirable and the process of actuating cam 108, translating base 102, and releasing cam 108 can be repeated. In this way, cutting guide assembly 100 allows for a quick and easy selection (and reselection) of a position of base 102 to insert 104. This can increase procedural efficiency, saving time and cost.

Figure 8B:
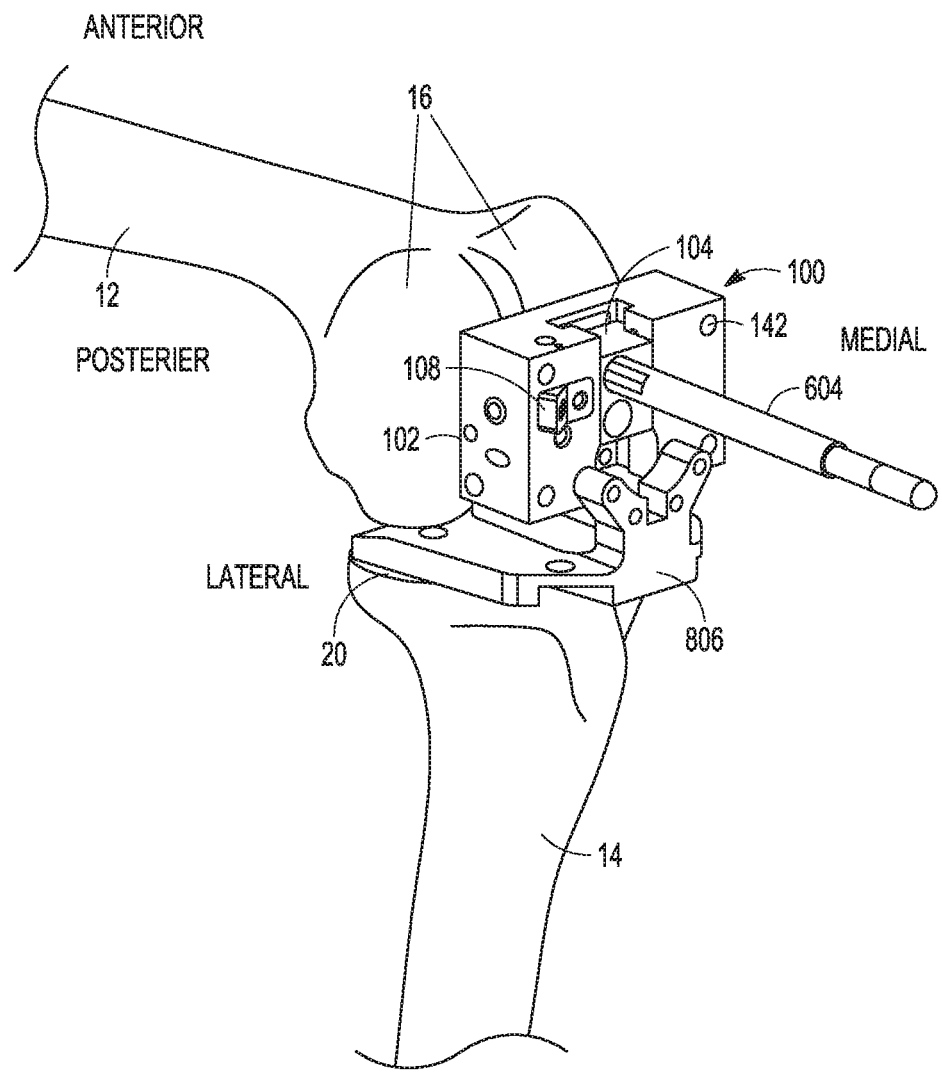
FIG. 8B shows an isometric view of a femur and a tibia with a tibia rotation block, in accordance with at least one example of the present disclosure

FIG. 8B shows an isometric view of femur 12 and tibia 14 with a tibia rotation block and cutting guide assembly 100 secured to the intramedullary rod 604, in accordance with at least one example of the present disclosure. Cutting guide assembly 100 can be consistent with the above description of cutting guide assembly 100.

In operation of some examples, ligament balancing can be achieved through rotation of cutting guide assembly 100 by securing tibia rotation block 806 to base 102 of cutting guide assembly 100. A desired external rotation of cutting guide assembly 100 of about 3° can be obtained automatically through correct balance and tension of the ligament system, in some examples. In some other examples, rotation can also be checked via the epicondylar axis using medial and lateral pins secured to base 102.

Figure 9A:
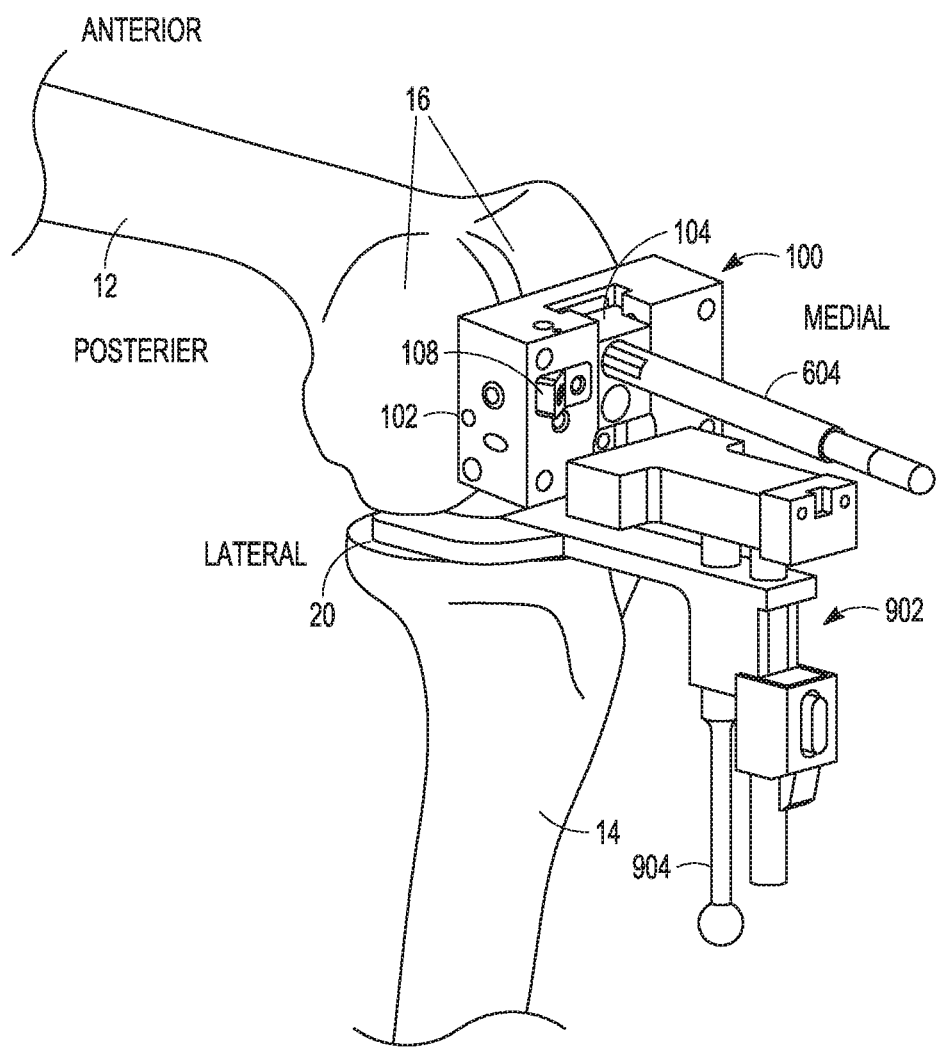
FIG. 9A shows an isometric view of a femur and a tibia with a ligament tensioner, in accordance with at least one example of the present disclosure.

FIG. 9A shows an isometric view of a femur and a tibia with ligament tensioner 902, in accordance with at least one example of the present disclosure. Ligament tensioner 902 can be a tensioner or balancer insertable between femur 12 and tibia 14. In operation of some examples, tensioner 902 can be actuated at tool interface 904 to increase or decrease tension of soft tissues of the knee joint. After a desired tension in achieved, tensioner 902 can be disengaged from the knee joint.

Figure 9B:
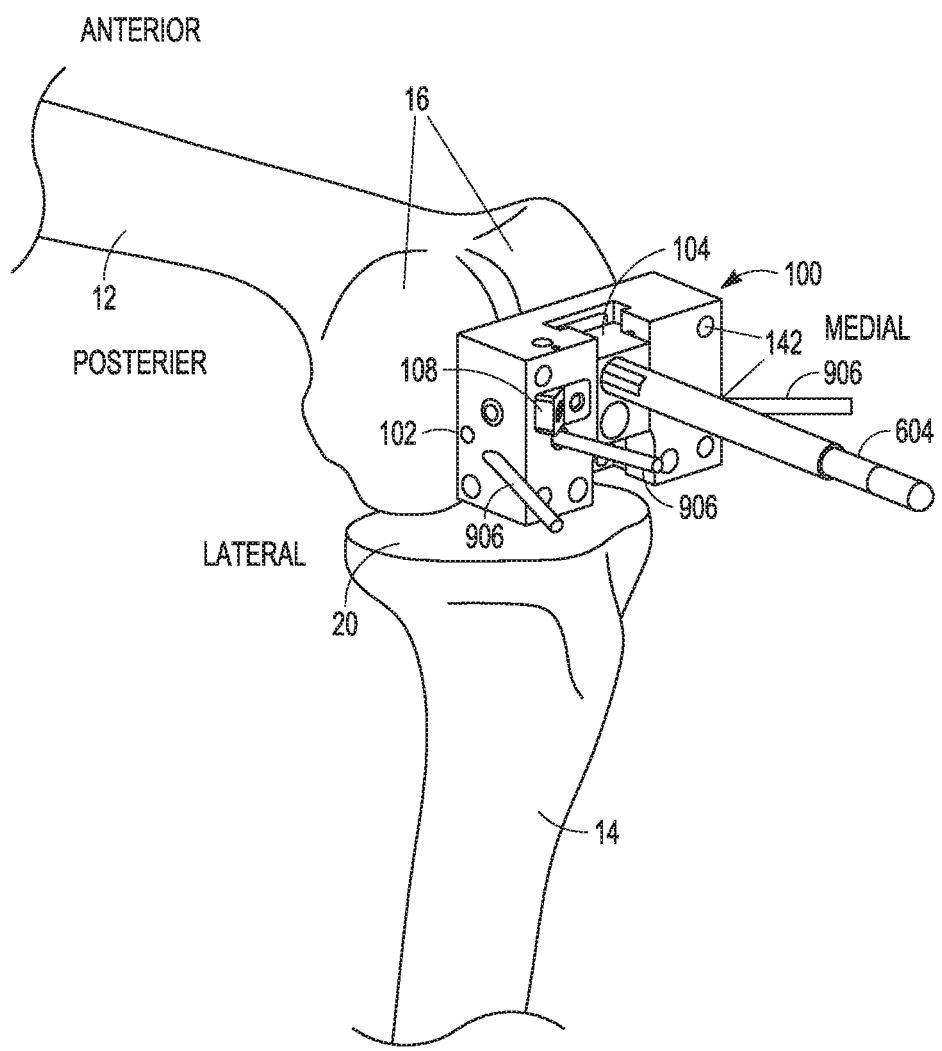
FIG. 9B shows an isometric view of a femur and a tibia with pins securing the guide to the femur, in accordance with at least one example of the present disclosure.

FIG. 9B shows an isometric view of a femur and a tibia with pins 906 securing cutting guide assembly 100 to femur 12, in accordance with at least one example of the present disclosure. In operation of some examples, a drill can be used to drill into a distal portion of femur 12 through pin bores 142 to create a bore in a distal portion of femur 12. Thereafter, pins 906, which can be Steinmann pins in some examples, can be inserted through pin bores 142 and into bores of the bone to temporarily secure base 102 to femur 12. Together with IM rod 604, pins 906 can reduce rotation of base 102 and insert 104 relative to femur 12 and can reduce translation of base 102 and insert 104 along an axis of IM rod 604.

Figure 10A:
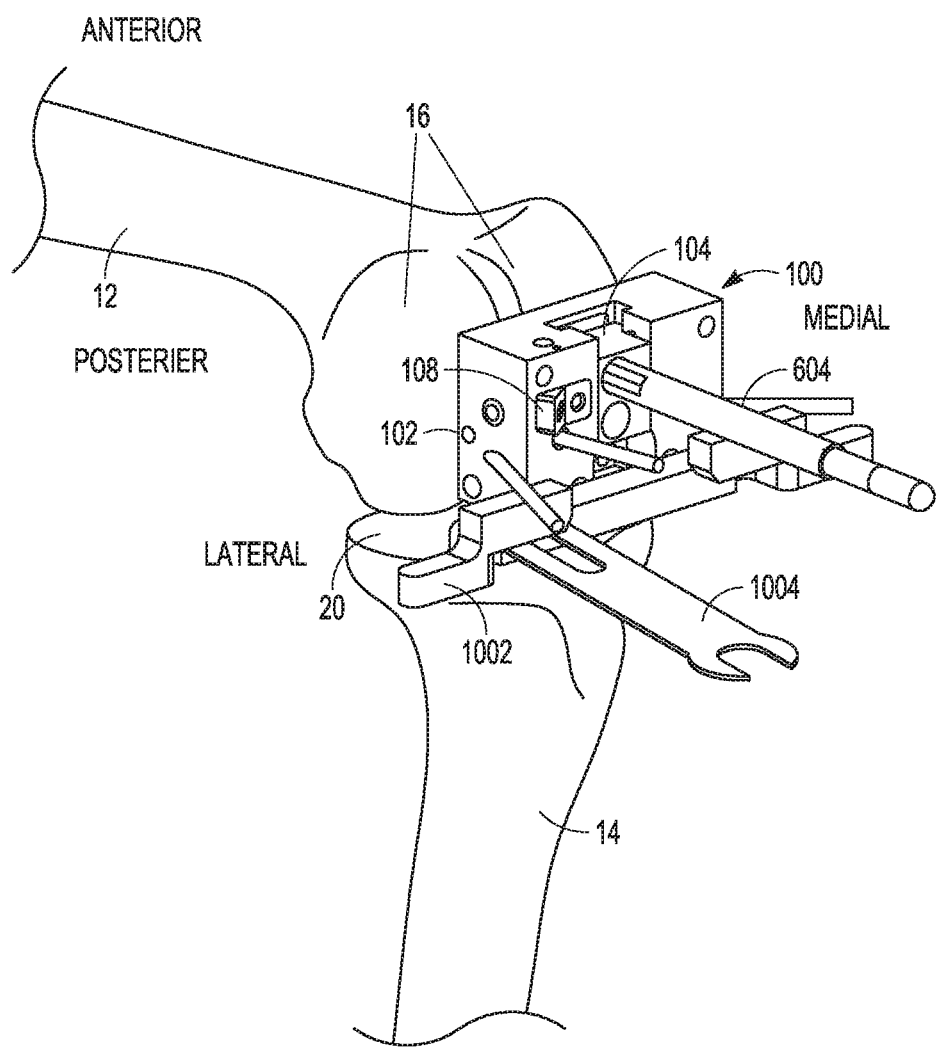
FIG. 10A shows an isometric view of a femur and a tibia with a cutting tool performing a cut of the femur, in accordance with at least one example of the present disclosure.

FIG. 10A shows an isometric view of femur 12 and tibia 14 with cutting tool 1004 performing a cut of femur 12, in accordance with at least one example of the present disclosure.

In some examples, posterior blade guide 1002 can be secured to a posterior portion of base 102. Posterior blade guide 1002 can include a blade slot sized to receive cutting tool 1004. The blade slot can limit movement of cutting tool 1004 to translation substantially perpendicular to the anterior-posterior plane, so that only a substantially planar cut of the posterior portion of femur 12 can be made with cutting tool 1004.

Figure 10B:
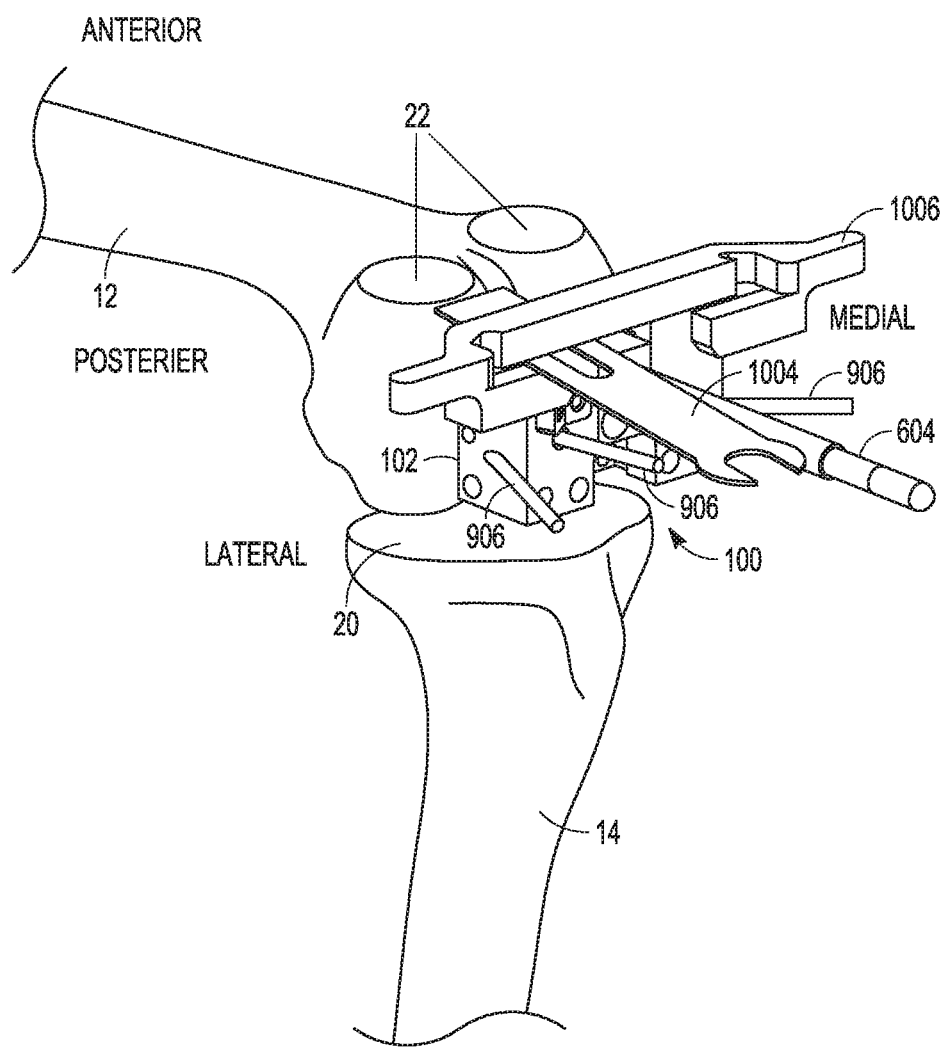
FIG. 10B shows an isometric view of a femur and a tibia with a cutting tool performing a cut of the femur, in accordance with at least one example of the present disclosure.

FIG. 10B shows an isometric view of femur 12 and tibia 14 with cutting tool 1004 performing cut 22 of femur 12, in accordance with at least one example of the present disclosure.

In some examples, anterior blade guide 1006 can be secured to an anterior portion of base 102. Anterior blade guide 1006 can include a blade slot sized to receive cutting tool 1004. The blade slot can limit movement of cutting tool 1004 to translation perpendicular to the anterior-posterior plane, so that a substantially planar cut of the posterior portion of femur 12 can be made with cutting tool 1004. In some examples, cutting tool 1004 can be operated to create anterior femoral cuts 22 in femur 12.

Figure 10C:
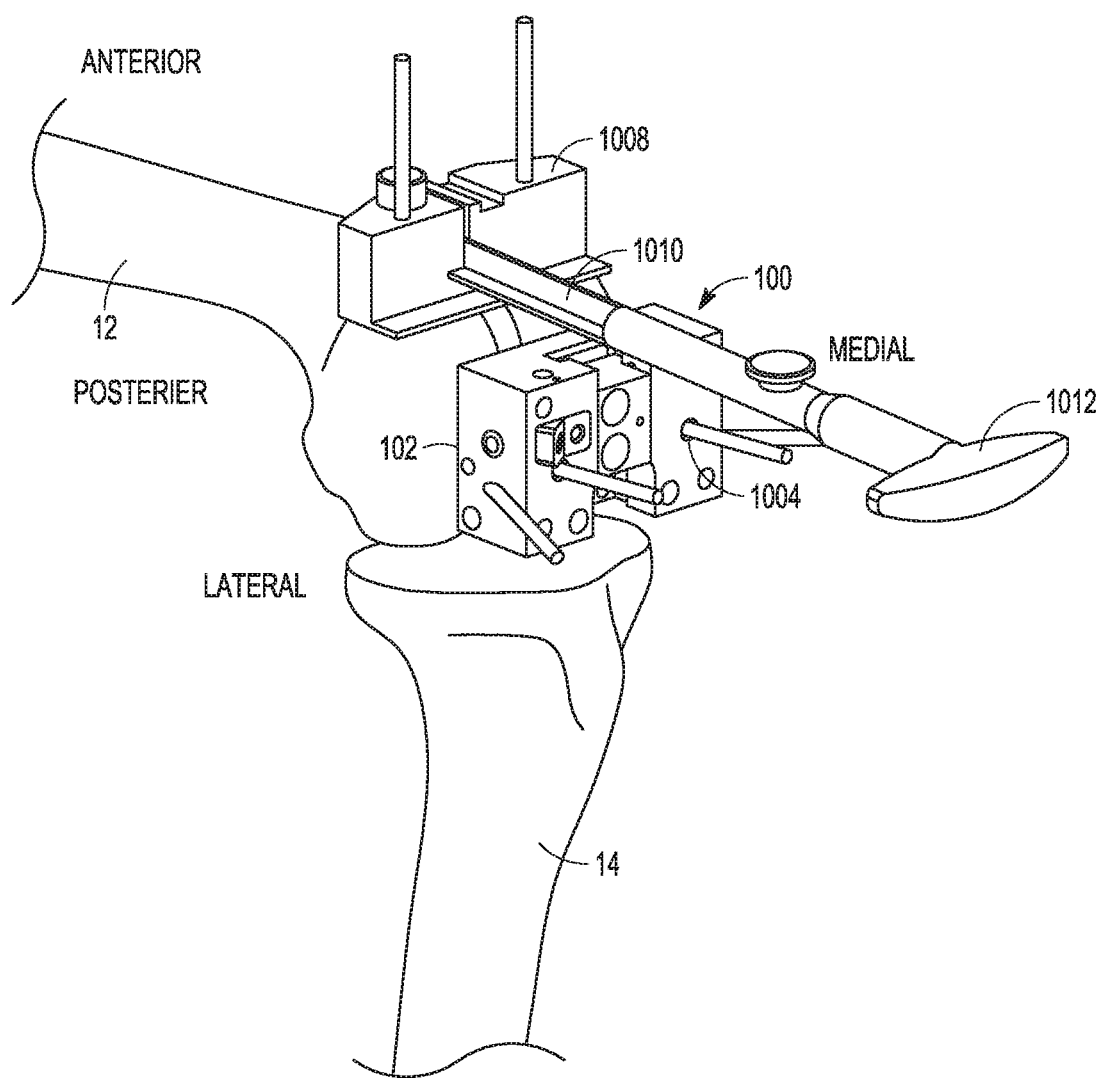
FIG. 10C shows an isometric view of a femur and a tibia with a secondary cutting guide secured to the cutting block, in accordance with at least one example of the present disclosure.
Figure 11:
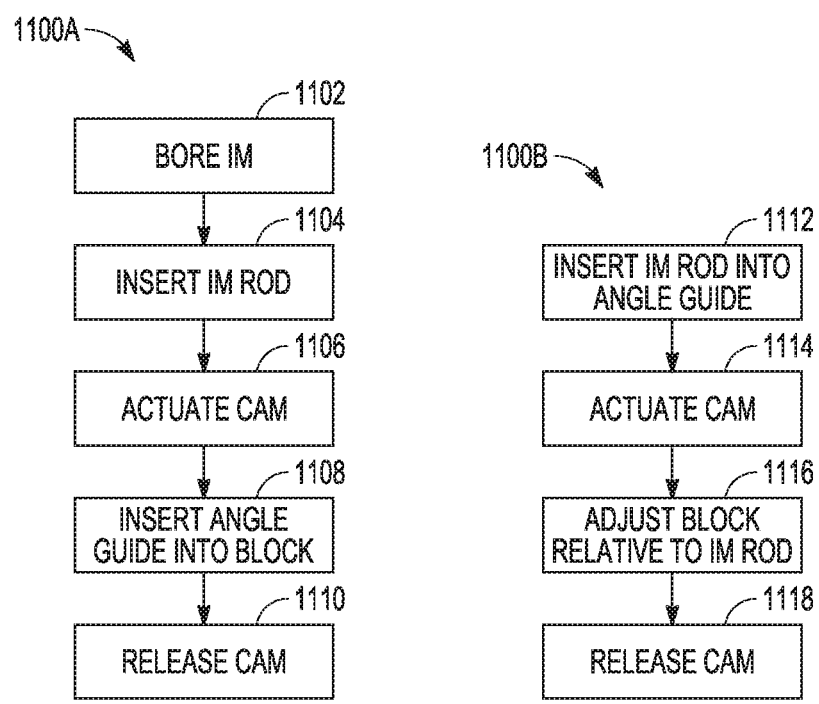
FIG. 11 shows a flow chart view of method 1100, in accordance with at least one example of the present disclosure.

FIG. 10C shows an isometric view of femur 12 and tibia 14 with secondary cutting guide 1008 secured to cutting guide assembly 100, in accordance with at least one example of the present disclosure.

Secondary cutting guide 1008 can be a distal cutting guide configured to guide a cutting tool for making a distal femoral cut. In operation of some examples, outrigger 1010 can be securable to base 102. Outrigger 1010 can then be used to position distal cutting guide 1008 relative to base 102 and therefore relative to femur 12. Once distal cutting guide 1008 has been placed as desired and secured to femur 12, removal tool 1012 can be secured to base 102 and can be used to remove cutting guide assembly 100 and outrigger 1010 from femur 12 so that a distal femoral cut can be performed using distal cutting guide 1008.

FIG. 10 shows a flow chart using the devices and systems described above, in accordance with at least one example of this disclosure. The steps or operations of the method of FIG. 10 are illustrated in a particular order for convenience and clarity. Many of the discussed operations can be performed in a different sequence or in parallel, and some operations may be excluded, without materially impacting other operations. The method of FIG. 10, as discussed, includes operations that may be performed by multiple different actors, devices, and/or systems. It is understood that subsets of the operations discussed in the method of FIG. 10 that are attributable to a single actor, device, or system could be considered a separate standalone process or method.

In operation of one example, method 1100 can begin with step 1102, where a femur (such as femur 12 of FIG. 6A) can be bored or drilled using a tool (such as drill bit 602 of FIG. 6A). At step 1104 IM rod 604 can be inserted into the bore and an intramedullary cavity of the femur. Then, at step 1106, cam 108 can be actuated to retract actuator 110 of cutting guide assembly 100, so that an angle guide (or insert 104) can be inserted into channel 106 of base 102 at step 1108 and also positioned relative to base 102. Once a desired position has been selected, cam 108 can be released, allowing actuator 110 to secure the position of insert 104 relative to base 102 at step 1110.

At step 1112, a bore of insert 104 (such as bore 112 or 114) and a central bore of base 102 can receive IM rod 604 therethrough. Cam 108 can then be actuated again at step 1114 to release the engagement between block 102 and insert 104. Base 102 can then be translated relative to insert 104 and IM rod 604 to position base 102 as desired relative to femur 12. Thereafter, cam 108 can be released to secure insert 104 relative to base 102.

In operation of some examples, steps 1106 through 1118 can be repeated in any order to position base 102 and insert 104, as desired. In operation of some examples, cam 108 can be actuated to remove base 102 and insert 104 from IM rod 604.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. An adjustable cut guide for resecting a bone, the cut guide comprising:
 a base comprising:
  a channel extending between a first end and a second end;
  a slot intersecting the channel;
  a cam extending into the slot, the cam coupled to the base within the slot to rotate between a first position and a second position;
  an actuator disposed in the slot, the actuator configured to linearly translate by rotation of the cam between an extended position when the cam is in the first position and a retracted position when the cam is in the second position; and
  an insert disposable within the channel of the base, the insert secured relative to the base by the actuator when the actuator is in the extended position, and the base translatable relative to the insert when the actuator is in the retracted position.

2. The adjustable cut guide of claim 1, wherein:
 the insert further comprises a rack including rack teeth; and
 the actuator further comprises teeth engageable with the rack teeth to secure the insert to the base when the actuator is in the extended position.

3. The adjustable cut guide of claim 2, wherein the teeth of the actuator disengage the rack teeth when the actuator is in the retracted position such that the base is free to move relative to the insert.

4. The adjustable cut guide of claim 3, the channel further comprising:
 a track configured to receive the rack of the insert, wherein the actuator teeth extend into the track to engage the rack of the insert when the actuator is in the extended position.

5. The adjustable cut guide of claim 1, further comprising:
 a biasing element engaging the actuator and the base within the slot, the biasing element biasing the actuator to an extended position and the cam to the first position.

6. The adjustable cut guide of claim 1, wherein the actuator further comprises a leg extending away from the cam into an anti-rotation slot of the base, the leg translatable in the anti-rotation slot with the actuator and the anti-rotation slot limiting rotation of the leg about an axis of the actuator.

7. The adjustable cut guide of claim 1, wherein the insert further comprises a first intramedullary bore disposed proximate an anterior portion of the insert and a second intramedullary bore disposed proximate a posterior portion of the insert.

8. A guide assembly for resecting a femur for a knee arthroplasty, the assembly comprising:
 a cut guide comprising:
  a base comprising:
   a channel extending between a first end and a second end;
   a slot intersecting the channel;
   a cam extending into the slot, the cam coupled to the base within the slot to rotate between a first position and a second position;
   an actuator disposed in the slot engageable with the cam, the actuator configured to linearly translate by rotation of the cam between an extended position when the cam is in the first position and a retracted position when the cam is in the second position; and
   an insert comprising an intramedullary bore, the insert engageable within the channel of the base, the insert secured relative to the base by the actuator when the actuator is in the extended position, and the base translatable relative to the insert between the first and second end when the actuator is in the retracted position; and
  an intramedullary rod insertable into the intramedullary bore of the insert and insertable into an intramedullary cavity of a bone.

9. The guide assembly of claim 8, the cut guide further comprising:
 a plurality of bores extending through the base substantially parallel to the intramedullary bore of the insert.

10. The guide assembly of claim 8, wherein the channel is configured to accept a plurality of inserts including the insert, wherein each of the plurality of inserts comprises an intramedullary rod bore having a rod angle between 1 degree and 9 degrees.

11. The guide assembly of claim 8, wherein the cut guide is an anterior/posterior cutting block for resection of a distal portion of a femur.

12. The adjustable cut guide of claim 8, wherein translation of the base relative to the insert and the intramedullary rod provides an anterior to posterior adjustment of the base relative to the bone.

13. The adjustable cut guide of claim 8, the body further comprising:
 a plurality of pin apertures extending through the body configured to receive pins therethrough to fixate the base to the bone.

14. The adjustable cut guide of claim 8, wherein the body is configured to receive at least one of a ligament tensioner and an anterior outrigger.

15. An adjustable cut guide for resecting a bone, the cut guide comprising:
 a base comprising:
  a channel extending between a first end and a second end;
  a slot intersecting the channel;
  a cam extending into the slot, the cam coupled to the base within the slot to rotate between a first position and a second position;
  an actuator disposed in the slot, the actuator translatable by rotation of the cam between an extended position when the cam is in the first position and a retracted position when the cam is in the second position, the actuator including teeth; and
  an insert disposable within the channel of the base, the insert secured relative to the base by the actuator when the actuator is in the extended position, and the base translatable relative to the insert when the actuator is in the retracted position, the insert including a rack including rack teeth engageable with the actuator teeth to secure the insert to the base when the actuator is in the extended position.

16. The adjustable cut guide of claim 15, wherein the teeth of the actuator disengage the rack teeth when the actuator is in the retracted position such that the base is free to move relative to the insert.

17. The adjustable cut guide of claim 16, the channel further comprising:
 a track configured to receive the rack of the insert, wherein the actuator teeth extend into the track to engage the rack when the actuator is in the extended position.

18. The adjustable cut guide of claim 15, further comprising:
 a biasing element engaging the actuator and the base within the slot, the biasing element biasing the actuator to an extended position and the cam to the first position.

19. The adjustable cut guide of claim 15, wherein the actuator further comprises a leg extending away from the cam into an anti-rotation slot of the base, the leg translatable in the slot with the actuator and the slot limiting rotation of the leg about an axis of the actuator.

* * * * *